(12) United States Patent
Shi

(10) Patent No.: US 7,346,989 B2
(45) Date of Patent: Mar. 25, 2008

(54) LOCK-TYPE DISPOSAL SAFE SURGICAL SCALPEL

(76) Inventor: Guoping Shi, No. 32, Xinlian Road, Pingjiang District, Suzhou City, Jiangsu Province (CN) 215008

( * ) Notice: Subject to any disclaimer, the term of this patent is extended or adjusted under 35 U.S.C. 154(b) by 283 days.

(21) Appl. No.: 10/671,149

(22) Filed: Sep. 23, 2003

(65) Prior Publication Data

US 2004/0236359 A1    Nov. 25, 2004

(30) Foreign Application Priority Data

May 21, 2003  (CN) ................................ 03 2 22103

(51) Int. Cl.
*A61B 17/32*  (2006.01)
(52) U.S. Cl. .................... 30/151; 30/162; 606/167
(58) Field of Classification Search ................ 30/151, 30/162, 335, 336; 24/629, 647, 655–657, 24/634, 632; 606/167
See application file for complete search history.

(56) References Cited

U.S. PATENT DOCUMENTS 3,106,004 A * 10/1963 Davis ........................... 24/632

| | | | | |
|---|---|---|---|---|
| 6,254,621 B1 * | 7/2001 | Shackelford et al. | ....... | 606/167 |
| 6,626,925 B2 * | 9/2003 | Newman et al. | ............. | 606/167 |
| 6,629,985 B1 * | 10/2003 | Kiehne | ........................ | 606/167 |

* cited by examiner

*Primary Examiner*—Stephen Choi
(74) *Attorney, Agent, or Firm*—Leonard Tachner

(57) ABSTRACT

A lock-type disposal safe scalpel comprising a blade (6), a handle (7) and a sheath (8). The sheath (8) is coupled to the handle (7) via a sliding mechanism and a positioning mechanism. The sheath (8) is provided with a button (1) and a locking block (2). A protective locking recess (3) and an operative locking recess (4) are provided on the front end of a sliding groove (5) of the handle (7) respectively. The button (1) is operated to press the locking block (2) so that the sheath (8) is slidably transferable between a position at the protective locking recess (3) and a position at the operative locking recess (4). A deadlock recess (12) is provided on the front end of protective locking recess (3) of the sliding groove (5), and the deadlock recess (12) is provided with a hindering mechanism so as to prevent the locking block (2) from disengaging, whereby the scalpel is brought into a deadlocked state. The sheath can be deadlocked to the handle when the sheath is operated to retreat back after use.

3 Claims, 5 Drawing Sheets

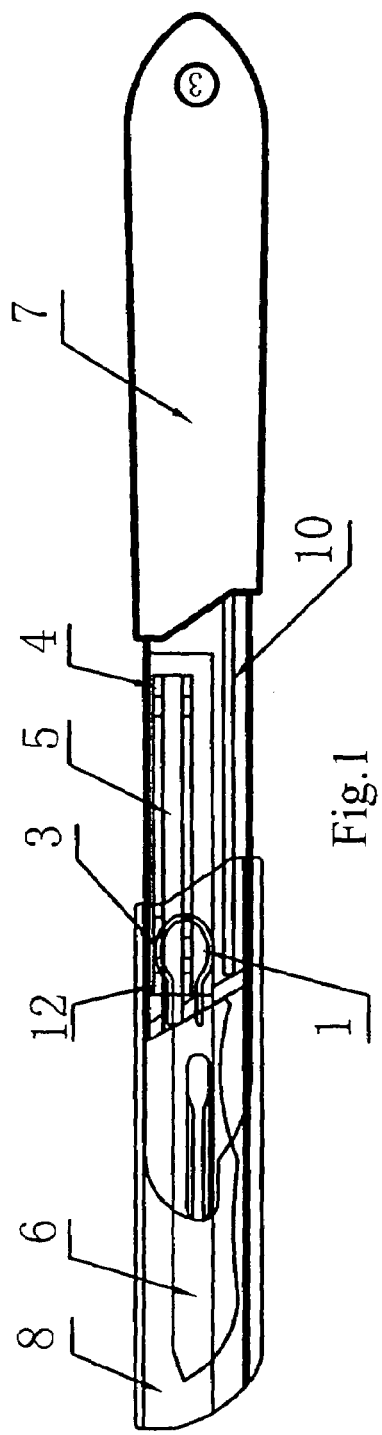
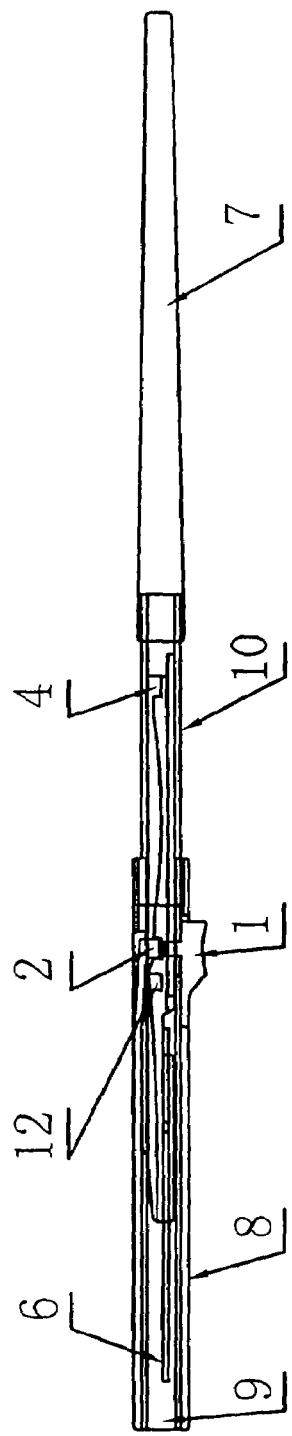
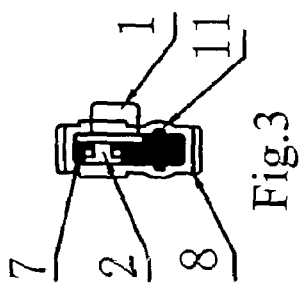
Fig.1
Fig.2
Fig.3

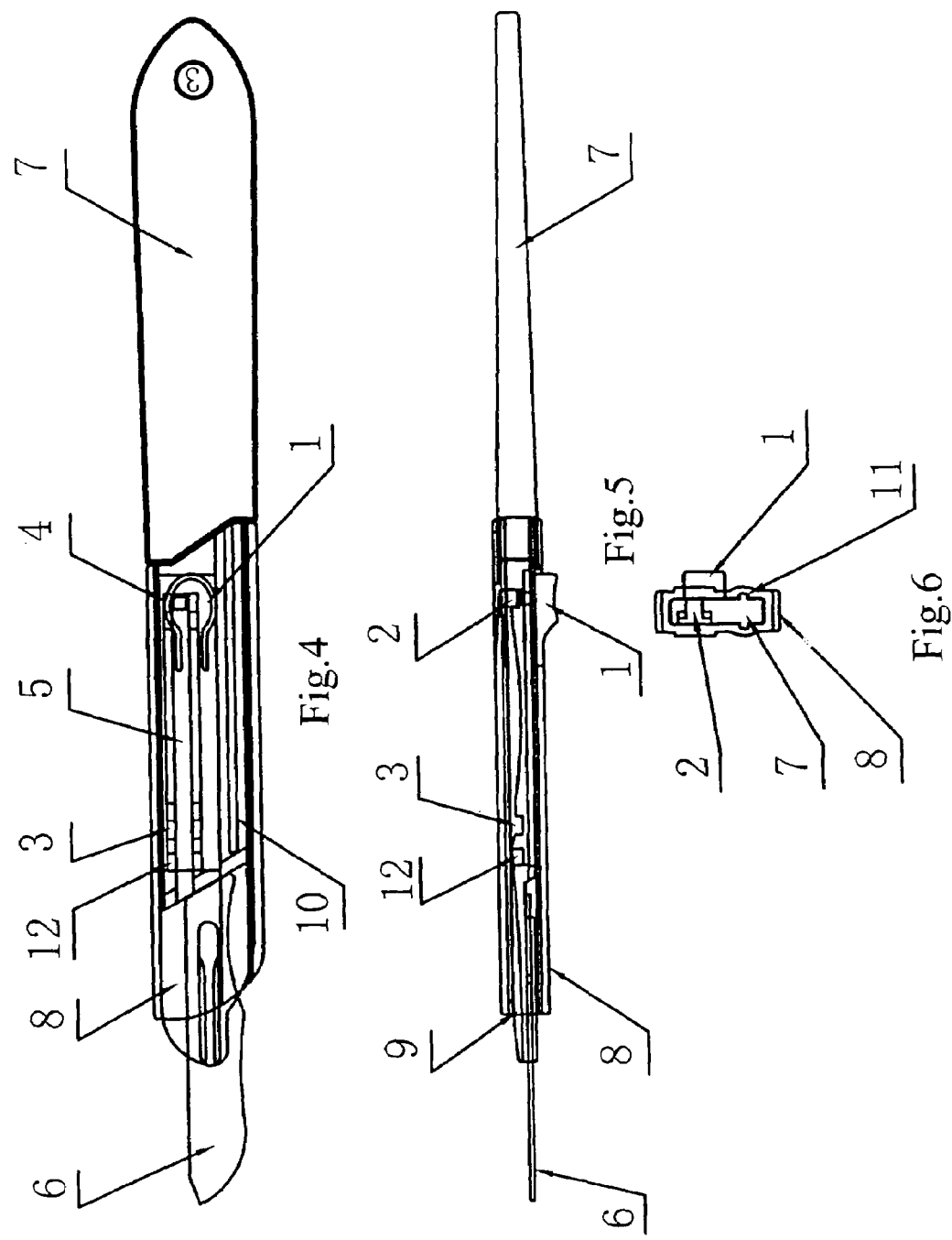

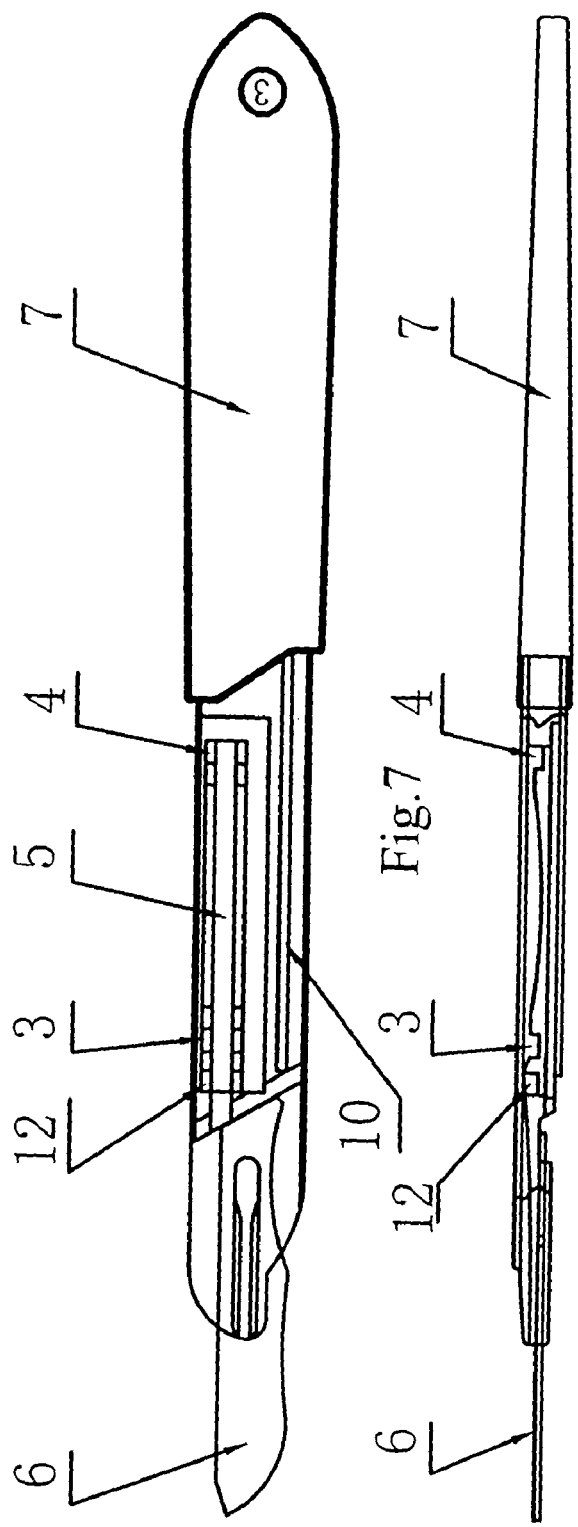
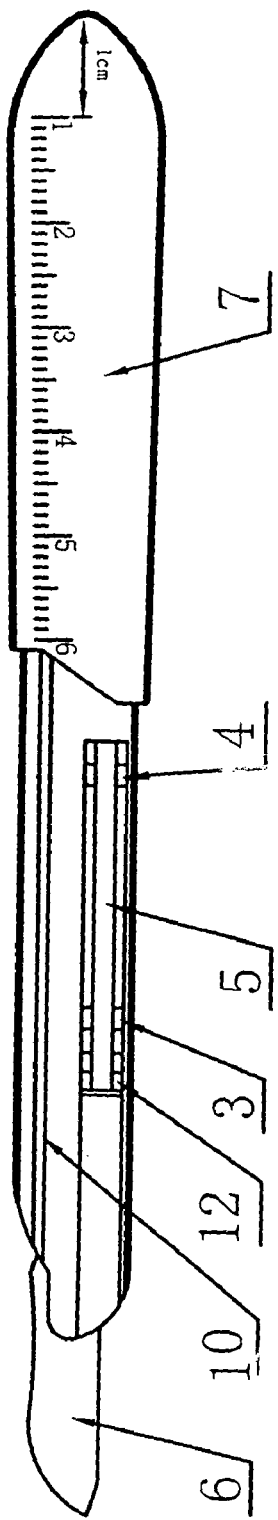
Fig.7　　Fig.8　　Fig.9

LOCK-TYPE DISPOSAL SAFE SURGICAL SCALPEL

CROSS-REFERENCE TO RELATED APPLICATION

This application claims priority from Chinese Utility Model Application No. 03222103.7 filed on May 21, 2003 in the State Intellectual Property Office of China, the disclosure of which is incorporated herein by reference.

BACKGROUND OF THE INVENTION

1. Field of the Invention

The present invention relates to a lock-type disposal safe surgical scalpel, more particularly, to a sheath-type scalpel having a plastic handle or a steel handle and including a disposal safe locking mechanism in which the sheath can be pushed to its deadlocked position after use of the scalpel so that reuse of the scalpel is prohibited.

2. Background Art

A scalpel as a surgical apparatus is widely used in surgical operations. With the rapid progress of the medical treatment, the problems of the safety of the scalpel are of much more concern at the present time. In view of the safety of the surgical scalpels, it is preferably advantageous to employ disposal safe scalpels. The disposal scalpels available nowadays, however, can be reused due to the deficiency of its configuration. As a result, such a scalpel may not be a safe surgical scalpel in a strict sense.

The Utility Model Patent No. CN 03220343.8 filed on Mar. 10, 2003 by the present applicant, has disclosed a slidable-sheath-type self-locking safe scalpel. The Utility Model has been made to solve the safety problem incurred from the blade of a conventional scalpel whose blade is configured to be exposed outside. More specifically, on one hand, medical treatment personnel may be hurt by a conventional scalpel when it is transferred during a surgical operation and a hazard of infectious diseases may subsequently occur. On the other hand, the safety problem remains after the scalpel is disposed of because the blade of the scalpel is exposed outside without protective means. As apparent from the above, the problem that it can be reused has not been solved in the conventional disposal scalpel. In fact, the sheath of the scalpel is opened prior to use and closed after use, however, the scalpel with this configuration can be opened again and reused.

SUMMARY OF THE INVENTION

Accordingly, it is an object of the present invention to provide a lock-type disposal safe scalpel in which a sheath can be pushed to its deadlock position to cause the scalpel to fail in operation so that reuse of it can be prohibited, thereby eliminating the safety problems resulting from the conventional sheath-type scalpel and realizing a disposal scalpel in a strict sense.

Additional aspects and advantages of the invention will be set forth in part in the description that follows, and in part, will be obvious from the description, or may be learned by the practice of the invention.

The foregoing and other objects of the present invention are achieved by providing a lock-type disposal safe scalpel, comprising: A blade, a handle and a sheath, said blade being secured in the front end of the handle, and said sheath being fit over the front end of the handle and being coupled to each other with a sliding mechanism and a positioning mechanism so that the blade is changeable between an exposed position where the blade extends outside through the opening at the front end of the sheath and a hidden position where the blade is hidden inside the sheath; wherein said positioning mechanism including a button, a locking block, a protective locking recess, an operative locking recess and a sliding groove; wherein said sliding groove being longitudinally provided on the handle, and the protective locking recess and the operative locking recess being provided on the front and back end of the sliding groove, respectively, the button and the locking block being configured to be associated plastic arms which extend from the front and back side of the sheath, respectively, the button presses against the locking block so that the locking block is transferable between a position at the protective locking recess and a position at the operative locking recess; and a deadlock recess is provided on the front end of protective locking recess of the sliding groove, and the deadlock recess is provided with a hindering mechanism so as to prevent the locking block from disengaging therefrom, thereby the scalpel is brought into a deadlocked state.

The preferred features and alternative embodiments will de described hereinafter:

In the above lock-type disposal safe scalpel, the sheath is engaged with the handle such that a slidable sheath is provided on the front end of the handle, and the blade is safeguarded and put into use by the sliding movement of the slidable sheath relative to the blade. The slidable sheath can be configured to be an integrated part, and can also be made of two separate pieces mated with each other.

Further, the hindering mechanism can be exemplified by the following construction:

(1) The hindering mechanism is formed by a side surface of the deadlock recess at the side of the protective locking recess. The bottom of the side surface is configured to be higher than a position where the locking block is disengaged so that the locking block cannot be disengaged by the operation of the button. More specifically, the disengaging side surface corresponding to the deadlock recess is elevated. As a result, the locking block can be disengaged from the deadlock recess when the button is pressed.

(2) The deadlock recess engages with the top portion at one side of the button so that a hindering mechanism is achieved. The top portion is configured to be higher than a position where the button is disengaged so that button cannot be pushed to its disengagement position. More specifically, the engaging surface of the button is elevated so that the button cannot be pressed downwards to effectively engage with the locking block.

(3) The hindering mechanism is achieved by a spacing wall, the spacing wall being provided in the deadlock recess so that the button and the locking block are separated from each other, thereby the button cannot touch the locking block. More specifically, the spacing wall is provided between the button and the locking block so that the two parts cannot engage with each other.

The characteristics and advantages of the present invention will be described as follows:

Firstly, a locking mechanism is provided on the front end of the protective locking recess so that the sheath can be deadlocked to the handle when the sheath is operated to retreat back after use. In this way, the safety problem related to the conventional sheath-type scalpel is completely solved.

Secondly, a locking mechanism is added to the conventional sheath-type scalpel including a sliding mechanism and a positioning mechanism. Due to this novel configuration, the reuse of the lock-type scalpel is prohibited and a disposal scalpel in a strict sense which can be used only once is achieved.

Thirdly, the lock-type disposal safe scalpel of the present invention has simplified construction, improved product reliability, and is advantageous in operation.

BRIEF DESCRIPTION OF THE DRAWINGS

The aforementioned objects and advantages of the present invention, as well as additional objects and advantages thereof, will be more fully understood hereinafter as a result of a detailed description of the preferred embodiments when taken in conjunction with the accompanying drawings in which:

FIG. 1 is a front view of the lock-type disposal safe scalpel according to an embodiment of the present invention, in which the sheath is configured to be transparent and the blade of the scalpel is in its hidden position;

FIG. 2 is a plan view of the lock-type disposal safe scalpel shown in FIG. 1;

FIG. 3 is a partially enlarged sectional view of the FIG. 1 showing the parts around the button;

FIG. 4 is a front view of the lock-type disposal safe scalpel according to an embodiment of the present invention, in which the sheath is configured to be transparent and the blade of the scalpel is in its exposed position;

FIG. 5 is a plan view of the FIG. 4;

FIG. 6 is a partially enlarged sectional view of the FIG. 4 showing the parts around the button;

FIG. 7 is front view of the lock-type disposal safe scalpel according to an embodiment of the present invention, in which the sheath is removed;

FIG. 8 is a plan view of the FIG. 7;

FIG. 9 is a back view of the FIG. 7;

Figure 10:
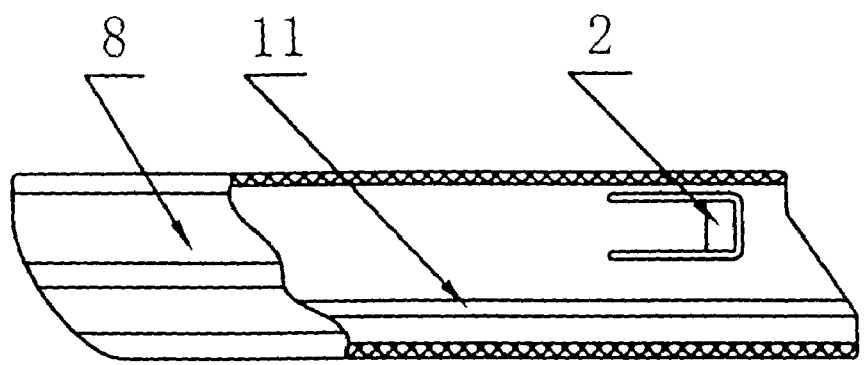
FIG. 10 is a front view of a slidable sheath of the lock-type disposal safe scalpel according to an embodiment of the present invention.
Figure 11:
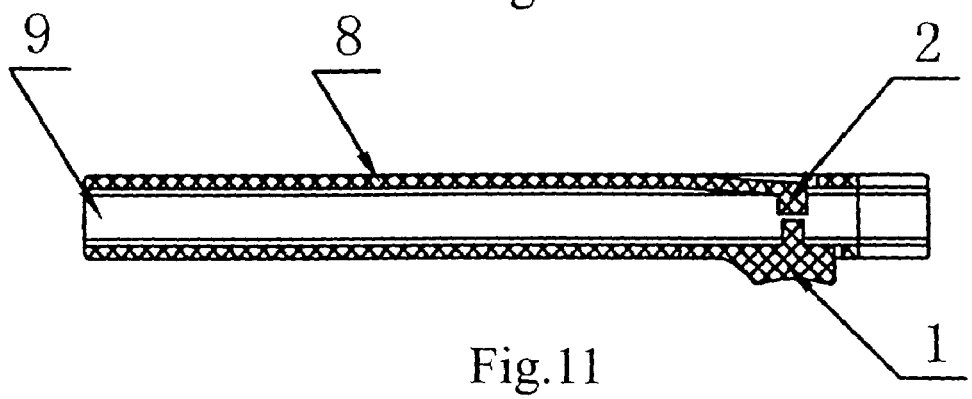
FIG. 11 is a plan view of the FIG. 10.
Figure 12:
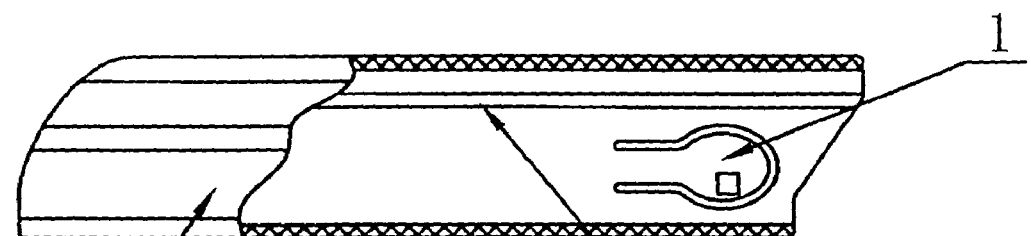
FIG. 12 is a back view of the FIG. 10.
Figure 13:
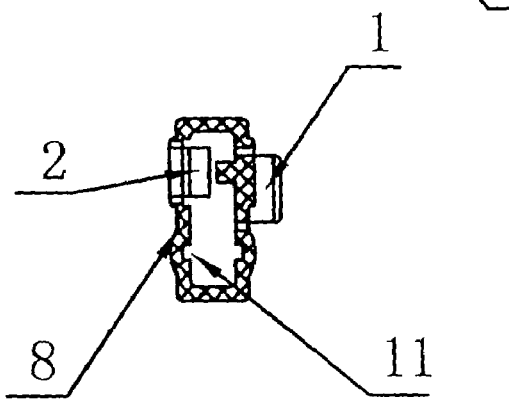
FIG. 13 is a left view of the FIG. 10.

In the drawings, the reference numeral 1 denotes a button; 2 denotes a locking block; 3 denotes a protective locking recess; 4 denotes an operative locking recess; 5 denotes a sliding groove; 6 denotes a blade; 7 denotes a handle; 8 denotes a sheath; 9 denotes an opening; 10 denotes a projection rib; 11 denotes a recess; 12 denotes a 5 deadlock recess; 13 denotes a side surface; 14 denotes a bottom; 15 denotes a top portion and 16 denotes a spacing wall.

DETAILED DESCRIPTION OF THE PREFERRED EMBODIMENTS

A preferred embodiment of the present invention will be described hereinafter in detail with reference to the attached drawings, wherein the like reference numerals refer to the like elements throughout. The present invention may, however, be embodied in many different forms and should not be construed as being limited to the embodiment set forth herein; rather, this embodiment is provided so that the present disclosure will be thorough and complete, and will fully convey the concept of the invention to those skilled in the art.

EXAMPLE 1

Referring to FIGS. 1-14, the lock-type disposal safe scalpel according to an embodiment of the present invention comprises a blade 6, a handle 7 and a sheath 8. The blade 6 is fixedly attached to the front end of the handle 7 as shown in FIGS. 7, 8 and 9. The handle 7 is made of plastic materials, and the sheath 8 is provided on the front end of an outer layer of the handle 7. The sheath 8 is fit over the front end of the handle 7 so that the blade is hidden in the sheath 8 as shown in FIGS. 1 and 2. The slidable sheath can be made of a single part. Alternatively, it can be configured to be a combination of two separate pieces. In this case, a slidable sheath made by injection molding of transparent plastic is provided for the lock-type disposal safe scalpel. An opening 9 is provided at the front end of the sheath 8. The sheath 8 and the handle 7 are coupled to each other by the front and rear sliding positioning mechanism so that the blade 6 is selectively located between a hidden position and an exposed position.

The sliding positioning mechanism is composed of a sliding mechanism and a positioning mechanism. The sliding mechanism is achieved by engagement between the front outer edge of the handle 7 and the inner edge of the sheath 8. A projected rib 10 is provided longitudinally on the front side and backside of the front outer edge of the handle 7, and a corresponding recess 11 is provided on the inner edge of the sheath 8. The projected rib 10 cooperates with the recess 11 so as to provide a sliding guide mechanism, thus the slidable sheath is properly guided.

Figure 14:
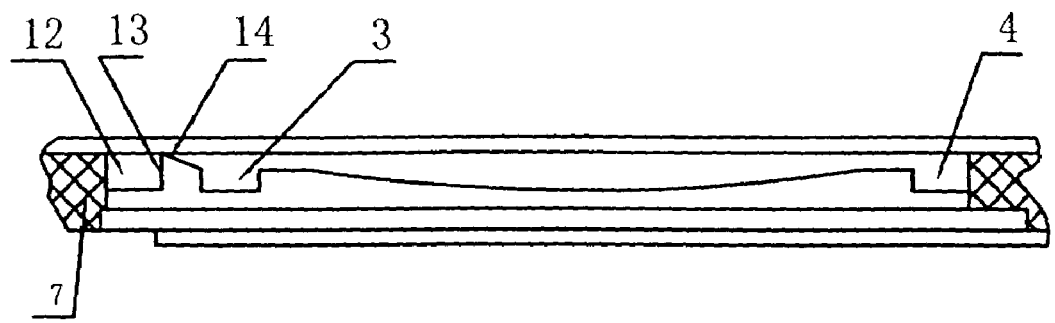
FIG. 14 is a schematic view of one example of the hindering mechanism of the lock-type disposal safe scalpel according to an embodiment of the present invention.

The positioning mechanism includes a button 1, a locking block 2, a protective locking recess 3, an operative locking recess 4, a deadlock recess 12 and a sliding groove 5. The sliding groove 5 is provided longitudinally along the handle 7 and is run through along the radial direction. The deadlock recess 12, the protective locking recess 3 and the operative locking recess 4 are sequentially provided on the first front, second front and back position of the front side and back side of the sliding groove 5. The button 1 and the locking block 2 are configured to be elastic arms which extend from the front and backside of the sheath 8, respectively. The engaging portions of the button 1 and the locking block 2 are opposite to each other and extend into the sliding grooves. The locking block 2 is slidably transferable between a position at the protective locking recess 3 and a position at the operative locking recess 4 due to the operation of the button 1. When the scalpel is put into use, the button is pressed downwards by the user's finger. Consequently, the engaging portion of the button 1 moves downwards so that the locking block 2 is disengaged from the protective locking recess 3 at the front end. Next, the button 1 is pulled backward and the sheath 8 moves backward until it reaches the position at the operative locking recess 4. Then, the button 1 is released and the locking block 2 is automatically locked at the position at the operative locking recess 4. At this time, the blade 6 extends outside the sheath through the opening 9 at the front end of the sheath 8 and is brought into an exposed state. After use, the button 1 is pressed downwards and the engaging portion of the button 1 moves downwards so that the locking block 2 is disengaged from the operative locking recess 4. Then, the button 1 is pushed forward and the sheath 8 slides forward until it reaches the position at the protective locking recess 3 where the locking block 2 is automatically locked in the position at the protective locking recess 3. At this time, the blade 6 is hidden in the sheath 8 and is brought into a protective state. During the sliding process of the sheath 8, the button 1 and the locking block 2 slide in the sliding groove 5 while the locking block 2 engages with the protective locking recess 3 and the operative locking recess 4 provided at the both sides of the front and back end of the sliding groove 5 by the projection at both sides thereof. In order to make sure that the sheath 8 cannot be opened again, the sheath 8 is pushed forward and then the button 1 and the locking block 2 are brought into the deadlock recess 12. The deadlock recess 12 is provided with a hindering mechanism so as to prevent the locking block 2 from disengaging from the deadlock recess 12, thereby the scalpel is brought into a deadlocked state. In the present embodiment, the deadlock recess 12 is formed by the side surface 13 at one side of the protective locking recess 3 so that a hindering mechanism is achieved. The bottom 14 of the side surface 13 is configured to have a greater height than the position where the locking block 2 is disengaged so that the locking block 2 cannot be disengaged by the button 1 as shown in FIG. 14.

EXAMPLE 2

Figure 15:
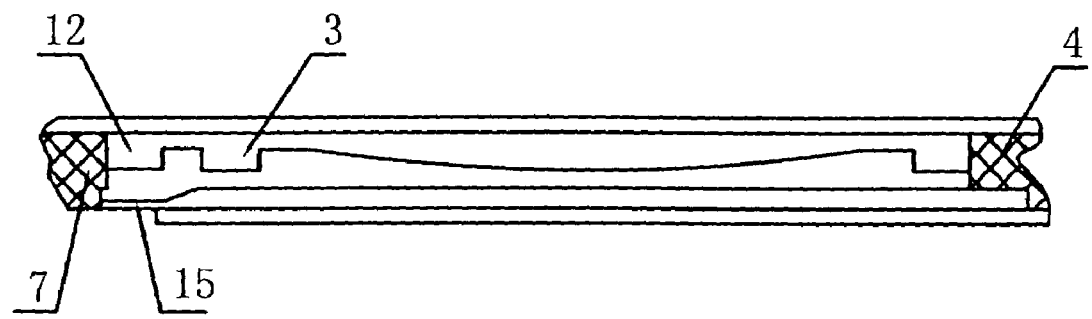
FIG. 15 is a schematic view of another example of the hindering mechanism of the lock-type disposal safe scalpel according to an embodiment of the present invention.

The FIG. 15 shows an alternative lock-type disposal safe scalpel according to another embodiment of the present invention. The lock-type disposal safe scalpel of example 2 is the same as that in the example 1 except that the hindering mechanism in the example 2 is different from the example 1. In this embodiment, the deadlock recess 12 corresponds to the top portion 15 at the side of the button 1 so that a hindering mechanism is achieved. The top portion 15 is configured to be higher than a position where the button 1 is disengaged so that the disengagement of the button 1 is prohibited. is prohibited.

EXAMPLE 3

Figure 16:
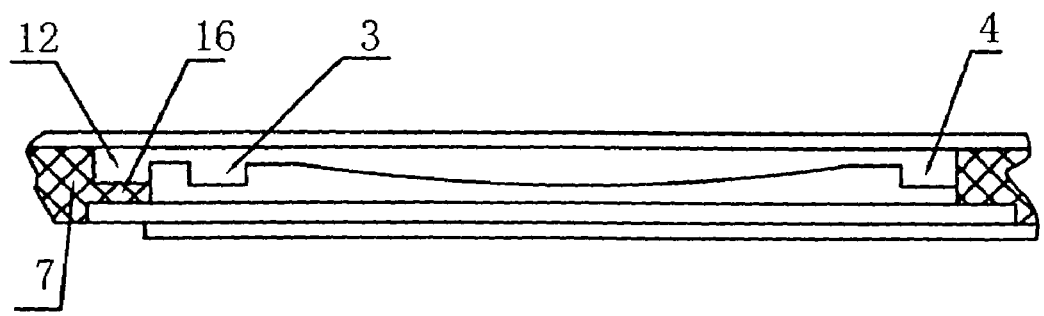
FIG. 16 is a schematic view of still another example of the hindering mechanism of the lock-type disposal safe scalpel according to an embodiment of the present invention.

The FIG. 16 shows an alternative lock-type disposal safe scalpel according to still another embodiment of the present invention. The lock-type disposal safe scalpel of example 3 is the same as that in the example 1 except that the hindering mechanism in the example 3 is different from the example 1. In this embodiment, the hindering mechanism is achieved by a spacing wall 16. The spacing wall 16 is provided in the deadlock 12 so that the button 1 and the locking block 2 are separated from each other, thereby the button cannot reach and press the locking block 2.

Although a few preferred embodiments have been shown and described, it would be appreciated by those skilled in the art that changes may be made in these embodiments without departing from the principles and spirit of the invention, the scope of the which is defined in the claims and their equivalents.

The invention claimed is:

1. A lock-type disposal safe scalpel, comprising:
a blade, a handle and a sheath, said blade being fixedly attached to a front end of the handle, said sheath being fit over the front end of the handle and coupled to the handle with a sliding mechanism and a positioning mechanism so that the blade is changeable between an exposed position where the blade extends outside through an opening at the front end of the sheath and a hidden position where the blade is hidden inside the sheath;
said positioning mechanism having a button, a locking block, a protective locking recess, an operative locking recess and a sliding groove;
said sliding groove being longitudinally provided on the handle, and the protective locking recess and the operative locking recess being provided on the front and back end of the sliding groove, respectively, the button and the locking block being configured to be associated with plastic arms which extend from the front and back side of the sheath, respectively, the button pressing against the locking block so that the locking block is transferable between a position at the protective locking recess and another position at the operative locking recess; and
a deadlock recess being provided on the front end of the protective locking recess of the sliding groove, and being provided with a hindering mechanism so as to prevent the locking block from disengaging therefrom, whereby the scalpel is brought into a deadlocked state;
wherein said hindering mechanism being formed by a side surface of the deadlock recess at the side of the protective locking recess, and the bottom of the side surface being configured to be higher than a position where the locking block is disengaged so that the locking block cannot be disengaged by the operation of the button.

2. A lock-type disposal safe scalpel, comprising:
a blade, a handle and a sheath, said blade being fixedly attached to a front end of the handle, said sheath being fit over the front end of the handle and coupled to the handle with a sliding mechanism and a positioning mechanism so that the blade is changeable between an exposed position where the blade extends outside through an opening at the front end of the sheath and a hidden position where the blade is hidden inside the sheath;
said positioning mechanism having a button, a locking block, a protective locking recess, an operative locking recess and a sliding groove;
said sliding groove being longitudinally provided on the handle, and the protective locking recess and the operative locking recess being provided on the front and back end of the sliding groove, respectively, the button and the locking block being configured to be associated with plastic arms which extend from the front and back side of the sheath, respectively, the button pressing against the locking block so that the locking block is transferable between a position at the protective locking recess and another position at the operative locking recess; and
a deadlock recess being provided on the front end of the protective locking recess of the sliding groove, and being provided with a hindering mechanism so as to prevent the locking block from disengaging therefrom, whereby the scalpel is brought into a deadlocked state;
wherein said hindering mechanism being formed by the deadlock recess corresponding to a top portion at the side of the button, the top portion being configured to be higher than a position where the button is disengaged so that the button cannot be pressed into its disengagement position.

3. lock-type disposal safe scalpel, comprising:
a blade, a handle and a sheath, said blade being fixedly attached to a front end of the handle, said sheath being fit over the front end of the handle and coupled to the handle with a sliding mechanism and a positioning mechanism so that the blade is changeable between an exposed position where the blade extends outside through an opening at the front end of the sheath and a hidden position where the blade is hidden inside the sheath;

said positioning mechanism having a button, a locking block, a protective locking recess, an operative locking recess and a sliding groove;

said sliding groove being longitudinally provided on the handle, and the protective locking recess and the operative locking recess being provided on the front and back end of the sliding groove, respectively, the button and the locking block being configured to be associated with plastic arms which extend from the front and back side of the sheath, respectively, the button pressing against the locking block so that the locking block is transferable between a position at the protective locking recess and another position at the operative locking recess; and a deadlock recess being provided on the front end of the protective locking recess of the sliding groove, and being provided with a hindering mechanism so as to prevent the locking block from disengaging therefrom, whereby the scalpel is brought into a deadlocked state;

wherein said hindering mechanism being formed by a spacing wall, the spacing wall being provided in the deadlock so that the button and the locking block are separated from each other, whereby the button cannot touch the locking block.

* * * * *